US006635027B1

(12) United States Patent
Cragg et al.

(10) Patent No.: US 6,635,027 B1
(45) Date of Patent: *Oct. 21, 2003

(54) METHOD AND APPARATUS FOR INTRAMURAL DELIVERY OF A SUBSTANCE

(75) Inventors: Andrew H. Cragg, Edina, MN (US); Edward L. Olson, Lake Forest, CA (US)

(73) Assignee: Micro Therepeutics, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/492,016

(22) Filed: Jan. 26, 2000

Related U.S. Application Data

(63) Continuation-in-part of application No. 09/079,487, filed on May 15, 1998, now Pat. No. 6,063,069.
(60) Provisional application No. 60/046,971, filed on May 19, 1997.

(51) Int. Cl.[7] .......................... A61B 17/20; A61M 25/00
(52) U.S. Cl. .......................................... 604/22; 604/264
(58) Field of Search ............................ 604/19, 22, 264, 604/96.01, 103.01, 103.07, 915, 916

(56) References Cited

U.S. PATENT DOCUMENTS

| 3,841,308 A | 10/1974 | Tate ........................... 128/2 M |
| 4,370,982 A | 2/1983 | Reilly ........................... 604/98 |

(List continued on next page.)

FOREIGN PATENT DOCUMENTS

| DE | 3921071 A1 | 2/1991 | ........... A61B/17/22 |
| DE | 39 41 949 | 6/1991 | ........... A61B/17/22 |

(List continued on next page.)

OTHER PUBLICATIONS

"Products for Regional Thrombolysis" MEDI–TECH Brochure (7 pp.) 1993.

(List continued on next page.)

*Primary Examiner*—Brian L. Casler
*Assistant Examiner*—Mark K. Han
(74) *Attorney, Agent, or Firm*—Joseph F. Breimayer (57) ABSTRACT

An infusion catheter is formed with a catheter lumen extending from a proximal end connector assembly to a distal end valve that is normally closed but is penetrable to allow introduction of a guidewire through the catheter lumen and distal end valve and to thereby allow advancement of the infusion catheter over the guidewire, thereby allowing access of a distal infusion segment to a wide number of locations in the body. A plurality of, closely spaced, side wall infusion holes infusion holes extend from the catheter lumen through the catheter side wall in a high strength, catheter distal end, infusion segment. A therapeutic or diagnostic substance is pumped in a pulsatile manner through the catheter lumen under high pressure after removal of the guidewire and closure of the distal end valve. The infusion segment is preferably moved back and forth as jets of the therapeutic or diagnostic substance are emitted. In one embodiment, the infusion catheter is used in thrombectomy methods and apparatus for removing a thrombus from a blood vessel by high velocity injection of a therapeutic or diagnostic substance, e.g., a plasminogen activator, through the side wall infusion holes as power lysis jets that lyse the adjacent thrombin. In another embodiment, the infusion catheter is used in intramural infusate injection, wherein a therapeutic or diagnostic lining penetration infusate is ejected from the infusion holes as a plurality of lining penetration jets that penetrate through a body vessel wall lining and intramurally into the body vessel wall.

22 Claims, 9 Drawing Sheets

U.S. PATENT DOCUMENTS

| | | | | |
|---|---|---|---|---|
| 4,661,094 | A | | 4/1987 | Simpson ................... 604/53 |
| 4,795,439 | A | | 1/1989 | Guest ..................... 604/43 |
| 4,968,306 | A | | 11/1990 | Huss et al. ............... 604/264 |
| 5,021,044 | A | | 6/1991 | Sharkawy .................. 604/53 |
| 5,085,635 | A | | 2/1992 | Cragg ..................... 604/96 |
| 5,087,244 | A | | 2/1992 | Wolinsky et al. ........... 604/53 |
| 5,112,305 | A | | 5/1992 | Barath et al. ............. 604/96 |
| 5,267,979 | A | | 12/1993 | Appling et al. ............ 604/247 |
| 5,279,546 | A | | 1/1994 | Mische et al. ............. 604/22 |
| 5,344,402 | A | | 9/1994 | Crocker ................... 604/96 |
| 5,370,609 | A | | 12/1994 | Drasler et al. ............ 604/22 |
| 5,370,653 | A | | 12/1994 | Cragg ..................... 606/170 |
| 5,380,273 | A | | 1/1995 | Dubrul et al. ............. 604/22 |
| 5,399,158 | A | | 3/1995 | Lauer et al. .............. 604/22 |
| 5,425,723 | A | | 6/1995 | Wang ...................... 604/280 |
| 5,474,530 | A | | 12/1995 | Pasafaro et al. ........... 604/22 |
| 5,496,267 | A | | 3/1996 | Drasler et al. ............ 604/22 |
| 5,505,729 | A | | 4/1996 | Rau ....................... 606/40 |
| 5,520,653 | A | | 5/1996 | Reilly et al. ............. 604/152 |
| 5,536,242 | A | | 7/1996 | Willard et al. ............ 604/30 |
| 5,554,114 | A | | 9/1996 | Wallace et al. ............ 604/53 |
| 5,569,275 | A | | 10/1996 | Kotula et al. ............. 606/159 |
| 5,611,775 | A | * | 3/1997 | Machold et al. ............ 604/103.01 |
| 5,713,848 | A | | 2/1998 | Dubrul et al. ............. 604/96 |
| 5,795,331 | A | | 8/1998 | Cragg et al. .............. 604/96 |
| 5,900,433 | A | | 5/1999 | Igo et al. ................ 514/530 |
| 5,951,517 | A | * | 9/1999 | Lampropoulos et al. ....... 604/151 |
| 5,954,706 | A | | 9/1999 | Sahatjian ................. 604/509 |
| 6,063,069 | A | * | 5/2000 | Cragg et al. .............. 604/508 |
| 6,152,141 | A | * | 11/2000 | Stevens et al. ............ 128/898 |
| 6,179,816 | B1 | * | 1/2001 | Mottola et al. ............ 604/264 |

FOREIGN PATENT DOCUMENTS

| | | | |
|---|---|---|---|
| DE | 43 42 205 | 12/1994 | ......... A61M/5/158 |
| EP | 0 470 781 A1 | 2/1992 | ......... A61B/17/22 |
| WO | WO 95/10232 | 4/1995 | ......... A61B/17/20 |
| WO | WO 96/01079 | 1/1996 | ......... A61B/17/20 |

OTHER PUBLICATIONS

"MicroMewi™ Multiple Sidehole Infusion Catheter", brochure, ©Micro Therapeutics, Inc. 1996, (1 pp.).

Patel, M.D., Nilesh H., "Deep Vein Thrombolysis", brochure, ©Micro Therapeutics, Inc. 1996, (1 pp.).

"Match Maker", brochure, ©Micro Therapeutics, Inc. 1996, ( 2 pp.).

"Products for Infusiopn Therapy", brochure, ©Cook, Inc. 1996 (7 pp.).

"Mewissen Infusion Catheter", brochure, ©Medi–Tech undated (1 pp.).

"Perfect Ending", brochure, ©Micro Therapeutics, Inc. 1995, (2 pp.).

Ritchie, J. L., et al., "Rotational approaches to atherectomy and thrombectomy", *Z. Kardiol.*, 76:Suppl. 6, 59–65 (1987).

Cragg M.D., Andrew H. et al., "New Developments in Thrombolytic Therapy", *Ninth Annual Int'l Symp. Vasc. Diag. & Interv.*, Jan. 27–30, 1997, pp. 83–86.

Werter MD et al., "Coronary Reperfusion with a New Catheter in Six Patients With Acute Occlusion After Angioplasty", *Cath. & Cardiovasc. Diag.*, 14:238–242 (1988).

"EDM Infusion Catheter", Peripheral Systems Group brochure ©1989, (3 pp.).

McNamara M.D., Thomas et al., "Coaxial system improves thrombolysis of ischemia", *Diagnostic Imaging*, (11/91) pp. 122–131.

MeWisson M.D., Mark W. et al., Symptomatic Native Arterial Occlusions: Early Experience with "Over–the–Wire Thrombolysis", *JVIR*, 1990; 1:43–47.

Hicks M.D., Marshall E., "Multilevel Infusion Catheter for Use with Thrombolytic Agents", *JVIR*, 1991; 2:73–75.

"Pulse*Spray® Pulsed Infusion Systems", AngioDyamics® 11/94 brochure (4 pp).

Bookstein M.D., Joseph J. et al., "Pulse–Spray Pharmacomechanical Thrombolysis", *Cardiovasc Intervent Radiol*, (1992) 15:228–233.

* cited by examiner

METHOD AND APPARATUS FOR INTRAMURAL DELIVERY OF A SUBSTANCE

This application claims the benefit of U.S. Provisional Application No. 60/046,971 filed May 19, 1997.

This application is a continuation-in-part of U.S. patent application Ser. No. 09/079,487 filed May 15, 1998, and titled METHOD AND APPARATUS FOR POWER LYSIS OF A THROMBUS, which issued as U.S. Pat. No. 6,063,069 on May 16, 2000.

FIELD OF THE INVENTION

The present invention relates generally to methods and apparatus for delivering a substance, e.g. a drug or therapeutic or diagnostic agent, into the wall of a blood vessel or other body duct or vessel from the lumen of the vessel through application of a fine spray or mist of the substance at a high velocity from a plurality of infusion holes distributed around a relatively short infusion segment of an infusion catheter body.

BACKGROUND OF THE INVENTION

The above-reference parent patent sets forth a discussion of the delivery of thrombolytic agents including plasminogen activators and heparin compounds through various types of catheters to dissolve blood clots or thrombi in native blood vessels and in vascular grafts and dialysis grafts. Such plasminogen activators include streptokinase, urokinase and tissue plasminogen activator (t-PA) and their analogues have been administered as lytic agents for lysis of arterial and venous thromboses. Such thrombolytic agents are delivered within the lumen of native blood vessels and in vascular grafts and dialysis grafts and that discussion is incorporated herein by reference.

Catheters have also been described that are designed to be employed to locally deliver a drug or therapeutic or diagnostic agent intramurally, that is into the wall of a blood vessel or other body duct or vessel, from the lumen of the vessel. Systemic administration of drugs treats the organism as a whole, even though the disease may be localized, such as injury to a body duct or vessel wall. Vessel walls are lined by a smooth lumen surface referred to as the endothelial layer that improves vascular blood flow hemodynamics and shields deeper vessel wall layers from contact with body fluids, e.g., blood in a blood vessel. Localized delivery of a drug intramurally into organ cavity walls, duct walls and blood vessel walls from the organ cavity or duct or vessel lumen poses special problems, since, by nature, the endothelial layers of such walls serve to transport and/or contain fluids within the organ cavity or duct or vessel lumen or transport systems.

Atherosclerotic disease causes localized occlusion of the blood vessels resulting from the build-up of plaque, and certain occlusion clearing treatment procedures and equipment can cause unintended injury to the blood vessel wall. Plaque deposits on an arterial wall effectively reduces the artery diameter and impede blood circulation past the deposits. Percutaneous transluminal coronary angioplasty (PTCA), or simply angioplasty, has proven to be a useful procedure for the treatment of localized atherosclerotic lesions (plaque deposits) of both coronary and peripheral vessels. Angioplasty involves the insertion of catheters, such as balloon catheters, through the occluded region of the blood vessel in order to mechanically expand a lumen through the occluded region by expansion of the balloon. A wide variety of atherectomy devices have also been proposed to open an occlusion and abrade or cut away the plaque deposits.

Unfortunately, successful atherectomy and PTCA invariably involves some interruption of the endothelial lining with a resulting violation of the barrier it provides between the deeper placed intima and smooth muscle cells (SMC) of the vessel wall and the blood itself. Local hemodynamic flow characteristics are also affected. The mechanical abrasion of the intima and the proliferation of smooth muscle cells stimulated by the atherectomy or PTCA procedure is believed to be responsible for restenosis, or closing of the vessel lumen that sometimes occurs. Restenosis may also occur as a result of clot formation due to an atherectomy or PTCA procedure caused injury to the vessel wall which triggers the natural clot-forming reactions of the blood.

It has been proposed that one method of combating restenosis might be the administration of various therapeutic agents known to block intimal and smooth muscle hyperplasia. The typical methods of intravascular medication involve the delivery of the medication systemically, either intravenously, or regionally (e.g., by intracoronary infusion). Systemic delivery is usually ill-suited to the treatment of conditions occurring at one or more discrete sites, because it involves the delivery of the medication to sites other than the target site, and it requires the infusion of large doses of the medication to assure the delivery of a therapeutic dose to the target site, thereby creating the possibility of deleterious effects. Another problem of systemic administration is the inevitable fluctuations of serum drug concentrations that it produces. The dosage that can be delivered to the target site may be limited by the need to minimize unwanted effects in other parts of the body. Furthermore, systemic delivery exposes the medication to possible degradation and elimination by the action of other bodily organs. For these reasons, systemically administered drugs such as anticoagulants, vasodilator, etc. have so far proven ineffective to prevent restenosis. More radical treatment involving agents such as cytostatic drugs or general enzyme blockers may prevent smooth muscle cell proliferation, but often these agents are toxic to humans at the levels necessary to effectively block development of the involved pathology.

Recently, site-specific drug delivery to the arterial wall has become a new strategy for the treatment of vascular diseases, including vessel restenosis following PTCA or atherectomy. These drug delivery systems include: (1) intravascular devices for site-specific (coronary artery) drug delivery comprising double-balloon catheters, porous balloon catheters, microporous balloon catheters, channel balloon catheters, balloon over stent catheters, hydrogel coated balloon catheters, iontophoretic balloon catheters and stent devices; (2) periadventitial and epicardial drug delivery devices, requiring surgical implantation, which include drug-eluting polymer matrices and a iontophoretic patch device; and (3) intramural injection of drug-eluting microparticles. See, for example, the descriptions of such devices appearing in U.S. Pat. Nos. 5,900,433, 5,954,706 and 5,112,305.

Drug delivery catheters of the perforated balloon type are disclosed, for example, in U.S. Pat. Nos. 5,087,244, 5,112,305 and 5,344,402. Catheters of these types have some drawbacks. For example, because the same fluid is used as the balloon inflation medium and as the drug medium, dilatation by balloon expansion is necessarily accompanied by drug delivery; neither function can be performed independently, which may be disadvantageous or inefficient in various clinical situations. Further inefficiency is engendered by the expulsion of the therapeutic agent before the balloon is fully expanded, so that the agent is not as forcefully administered to the luminal wall tissue as it would be if the balloon were fully expanded so as to bring it into close proximity or contact with the wall. A related problem is that the agent is typically expelled at relatively low pressures that are insufficient to effect any substantial degree of penetration of the lumen wall surface, thereby limiting the therapeutic effect of the agent in certain situations. Finally, in drug delivery PTA catheters in which the same fluid is used as the balloon inflation medium and the drug medium, the reversal of fluid flow to deflate the balloon may tend to draw blood into the catheter lumen, requiring it to be withdrawn for purging or replacement after a single use.

Direct injection of drugs from infusion ports of a catheter against the endothelial layer and into the vessel wall have also been proposed in commonly assigned U.S. Pat. No. 5,554,114. A catheter body without a balloon is provided that can be advanced in a straight configuration to the injured or diseased vessel site of and then transformed into a loose, helical distal infusion segment having infusion ports arranged toward the vessel wall.

Thus, problems remain however in the exact method by which the local administration of drugs or therapeutic agents should be accomplished. Conventional methods of drug therapy, as discussed above, often result in blood levels of the cytotoxic agent that are dangerous for the patient. Even with local administration of these agents, one must consider that the normal blood flow of the vessel vill dilute the local concentration of the therapeutic agent by a wash-out effect. The need remains, therefore, to devise a system whereby otherwise toxic therapeutic agents are concentrated and localized intramurally within the affected vessel wall segment.

In addition to the need for improved drug delivery to counter restenosis, there is a more general need in many branches of medicine for improved localized internal delivery of substances including therapeutic agents and drugs and diagnostic agents into the walls of ducts, organs and vessels. In particular, there is need for improved delivery into tissue and into cells themselves within organs, ducts, tracts and vessels of the body via percutaneous and luminal access.

SUMMARY OF THE INVENTION

The present invention relates to a number of approaches to satisfying these needs for delivering a substance or lining penetration infusate, e.g., a therapeutic agent or drug or diagnostic agent, intramurally into a localized section of the wall of a body vessel, duct, tract, vein, artery, or organ (herein body vessel).

In one embodiment of the invention, a selected bolus volume of such a substance (referred to herein as a lining penetration infusate) is injected at a selected flow rate into a high strength catheter lumen of an infusion catheter having a distal infusion segment formed in accordance with the present invention. The corresponding bolus volume is ejected or emitted through multiple side wall perforations or infusion holes closely spaced from one another in the relatively short infusion segment as high velocity, low volume, lining penetration jets that penetrate the adjacent endothelial layer. The catheter infusion segment is advanced through the localized section of interest, and the high velocity intramural penetration of the adjacent endothelial layer is repeated as necessary.

The fine, high velocity, lining penetration jets result from the injection of a bolus of lining penetration infusate having a prescribed fluid density at a selected pressure and injection rate of flow (volume per unit of time) into the catheter lumen which is controlled by a power injector. The outflow rate of lining penetration infusate from the infusion holes is proportional to the total number and size (i.e., the total outflow area) of the infusion holes in the infusion segment, the pressure applied to the bolus as it is injected, and other factors. The injected bolus of lining penetration infusate injected into the catheter lumen forces a corresponding fraction of the bolus through each infusion hole. The ejection velocity of the lining penetration jets is related to the outflow rate and inversely proportional to the total outflow area. The outflow rate is selected to maximize the velocity of the high velocity, lining penetration jets of infusate to ensure penetration of the lining penetration infusate into the interior layers of the wall of the body vessel.

The infusion holes are dense in the infusion segment, and the infusion segment is relatively short, between 0.2 cm to 2.0 cm long, to provide a thorough coverage of the section of the endothelial layer of the wall of the body vessel. For example, in one embodiment, 30 to 50 infusion holes are preferably provided per centimeter of length of the infusion segment and are evenly distributed around the circumference of the catheter body in each such cm of length. In another embodiment, the 20 to 32 infusion holes per linear centimeter are distributed in a helical pattern extending around the infusion segment and are closely spaced from one another. The high density spray of high velocity, lining penetration jets causes the section of endothelial lining surrounding or adjacent to the short, 0.2 cm to 2.0 cm long, infusion segment to be thoroughly penetrated.

In use, the lining penetration infusate preferably includes the a radiopaque material that can be observed under fluoroscopy as it is emitted from the infusion holes as fine, high velocity, lining penetration jets. The catheter infusion segment can be advanced back and forth in the section of the endothelial layer by the physician manipulating the proximal portion of the catheter during the emission of the lining penetration jets to distribute the intramurally delivered lining penetration infusate more evenly. The distribution of the radiopaque, lining penetration infusate can be observed under fluoroscopy or other radiographic imaging.

In relatively large body vessels, the distal infusion segment preferably incorporates a biasing mechanism operable from the catheter proximal end in a biasing state for biasing the catheter side wall and at least certain ones of the infusion holes of the infusion segment into close relation with the section of the vessel wall. Exemplary biasing mechanisms include a laterally inflatable asymmetric balloon or a laterally deployable wire or a coiled configuration of the infusion segment.

A number of advantages flow from the present invention. The present invention provides for a rapid intramural injection of lining penetration infusate as high velocity, lining penetration jets. The penetrable distal tip valve allows over-the-wire introduction of the catheter which is simple and allows access to a wide number of locations, e.g. through the abdominal aorta, the iliac, femoral popliteal and tibial blood vessels as well as small diameter cerebral blood vessels. The catheter employed is relatively inexpensive and disposable.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS

Figure 1:
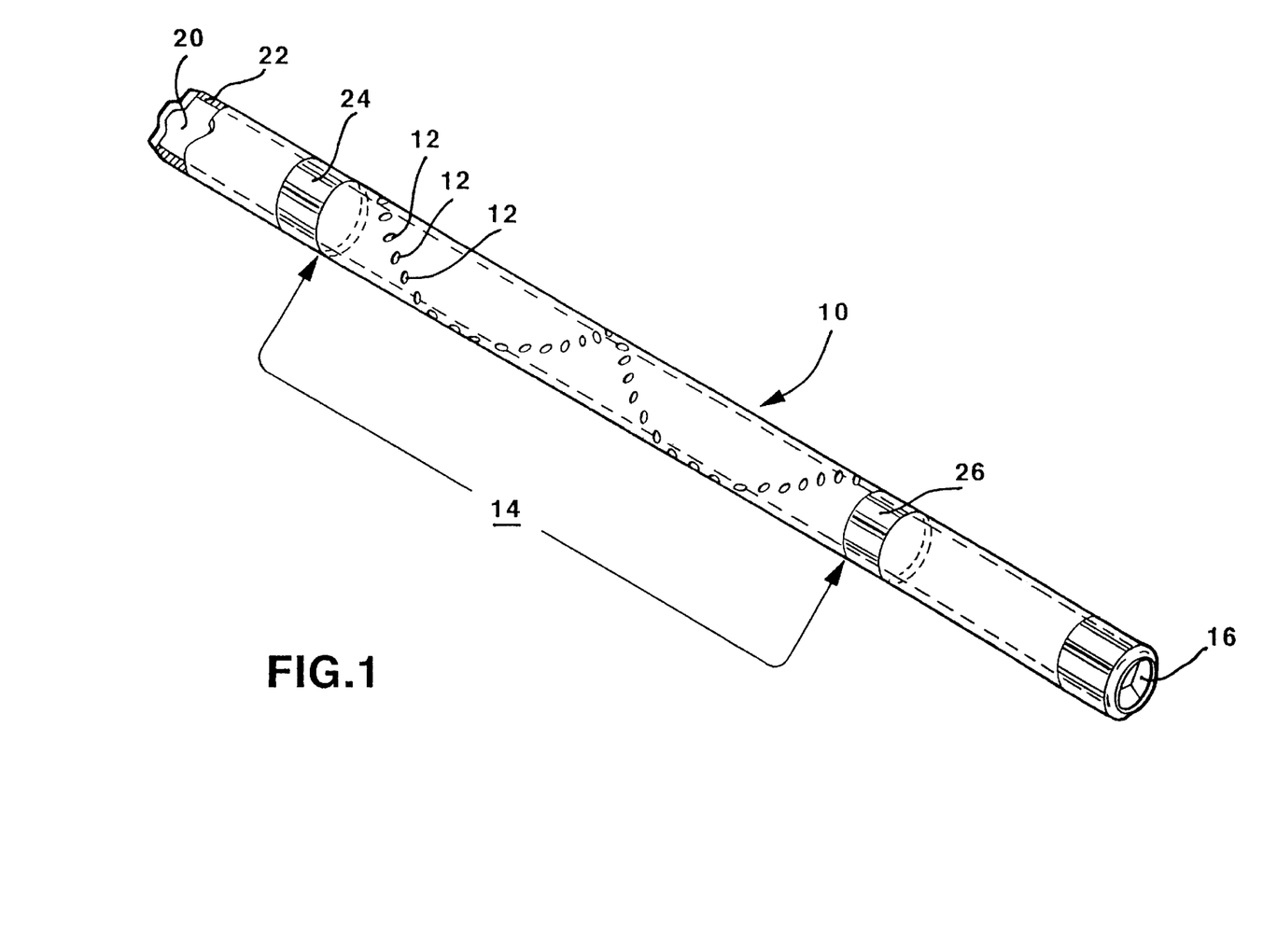
FIG. 1 is a perspective view of a first embodiment of an infusion catheter for power lysis and intramural delivery in accordance with a first embodiment of the present invention having a helical pattern of side wall infusion holes formed in the distal infusion segment.
Figure 9:
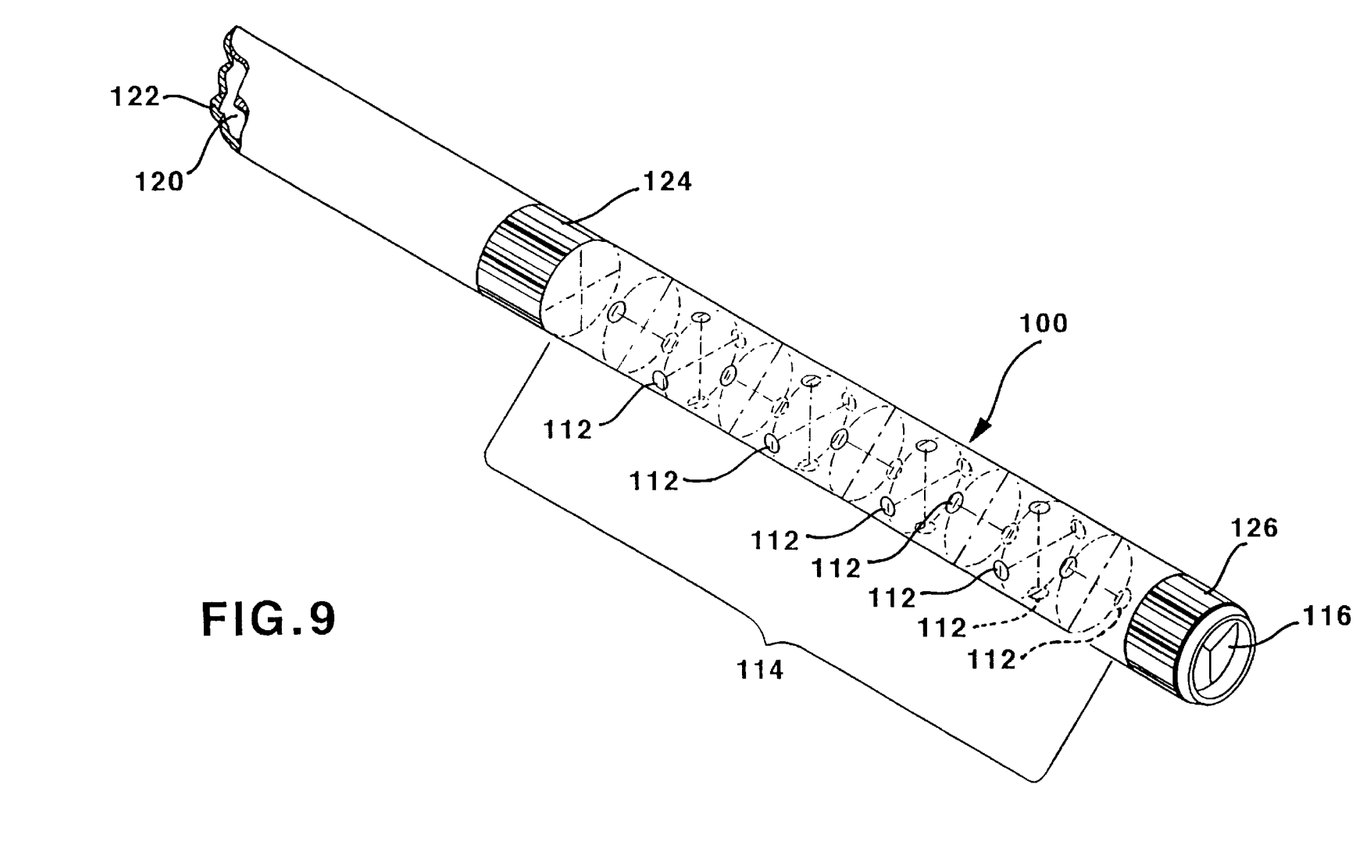
FIG. 9 is a perspective view of a further embodiment of an infusion catheter for power lysis and intramural delivery in accordance with a further embodiment of the present invention having a relatively uniform distribution of side wall infusion holes formed in the distal infusion segment.
Figure 10:
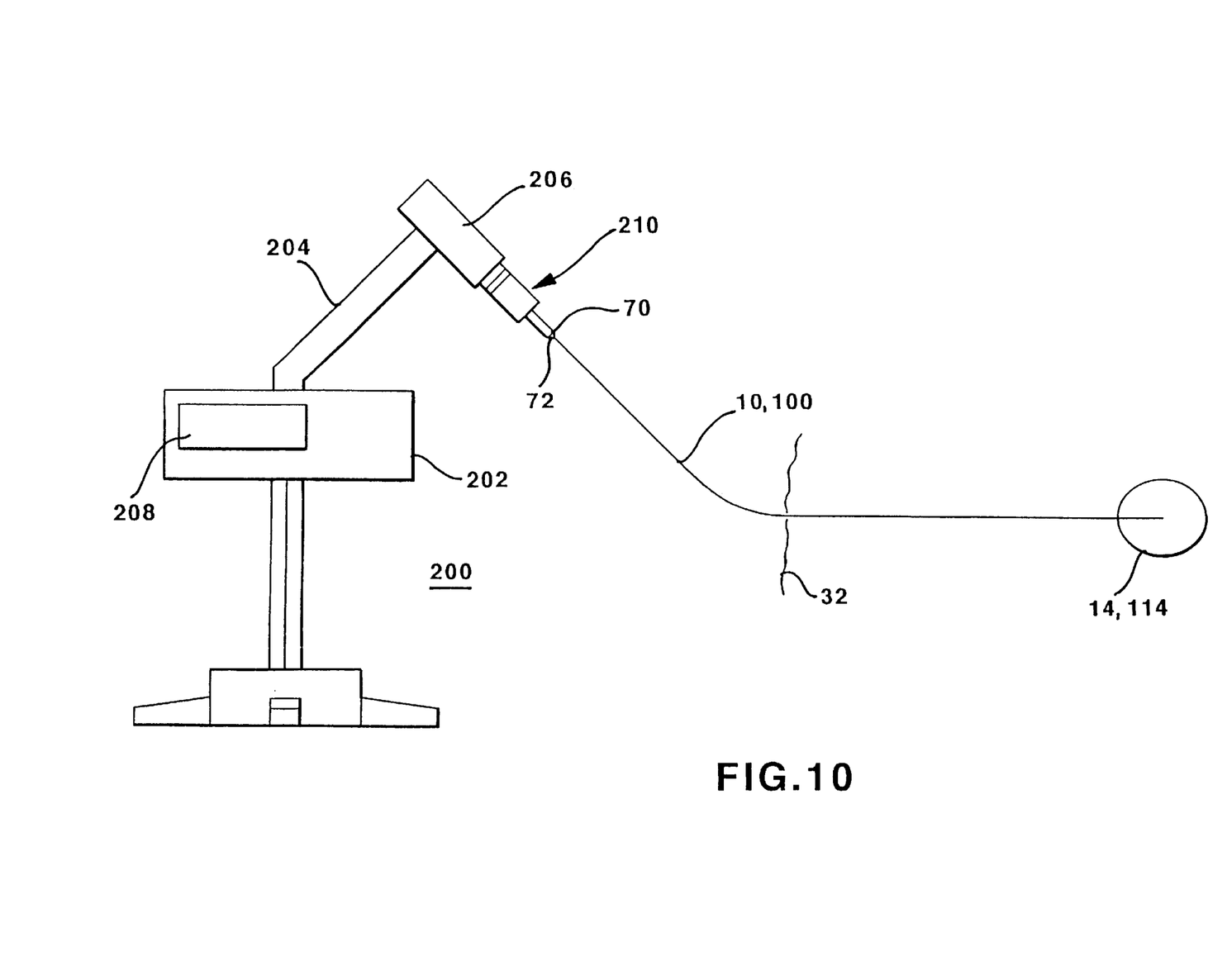
FIG. 10 is a simplified schematic illustration of a system for practicing the power lysis of thrombi and the intramural delivery of infusates in accordance with the present invention.
Figure 11A:
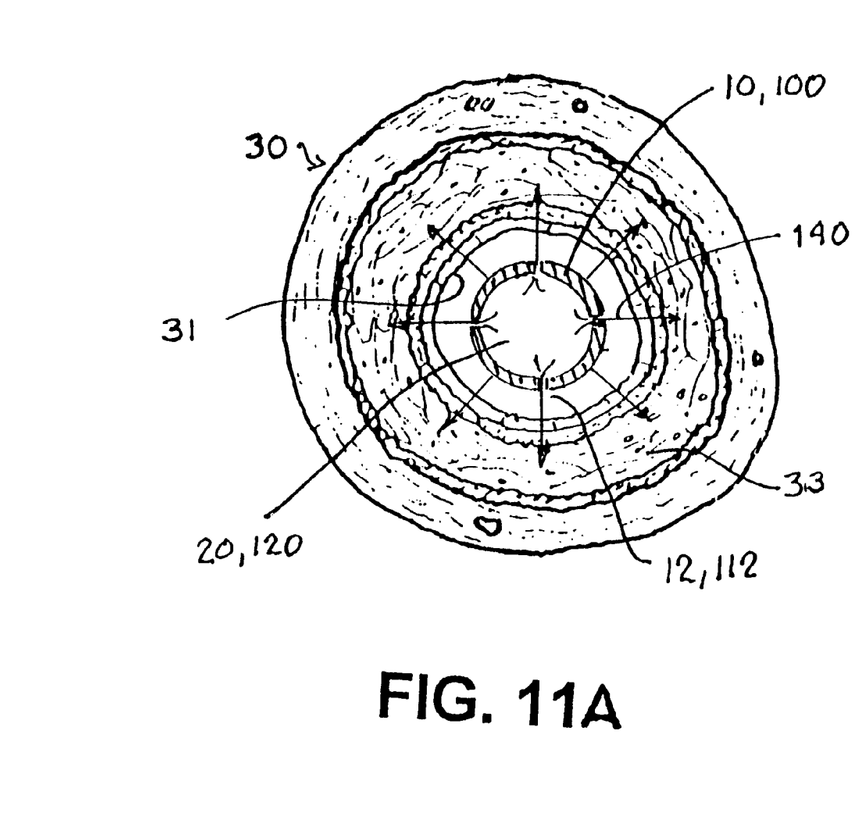
FIGS. 11a and 11b are simplified end views of the lining penetration jets emitted from the side wall infusion holes of the catheter of FIGS. 1 and 9 and penetrating into the endothelial lining of an artery and a vein, respectively.
Figure 11B:
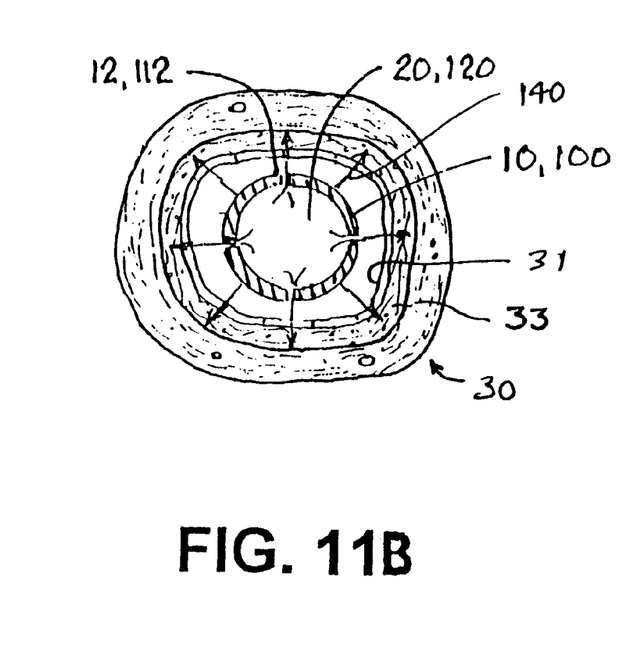
Figure 12:
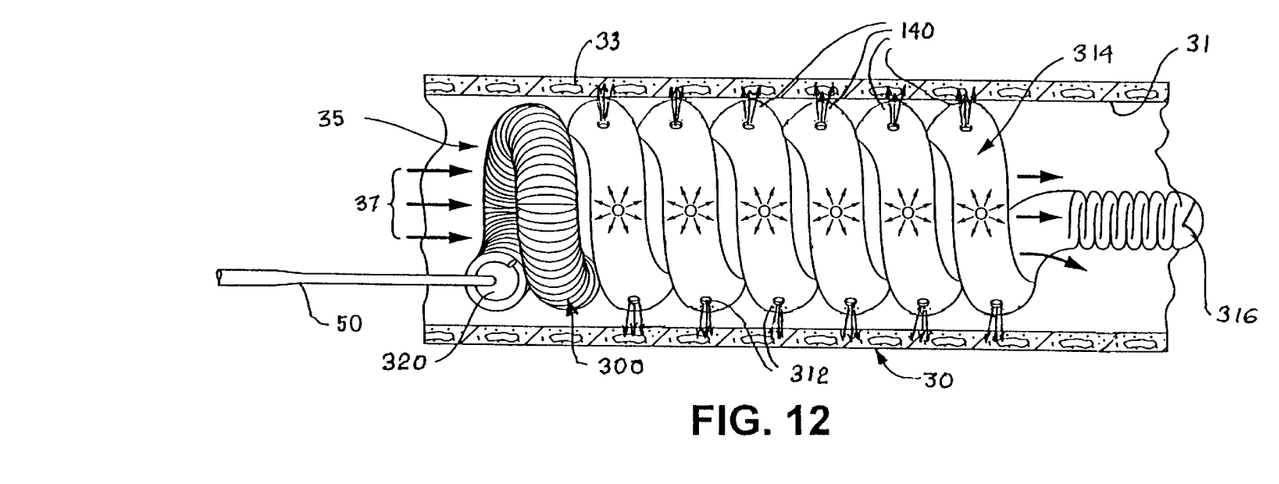
FIGS. 12 and 13 are views of further embodiments of a distal infusion segment configured with biasing mechanisms to enable situating the side wall infusion holes close to the endothelial lining of a large diameter body vessel to ensure penetration of the endothelial layer by the emitted lining penetration jets.
Figure 13:
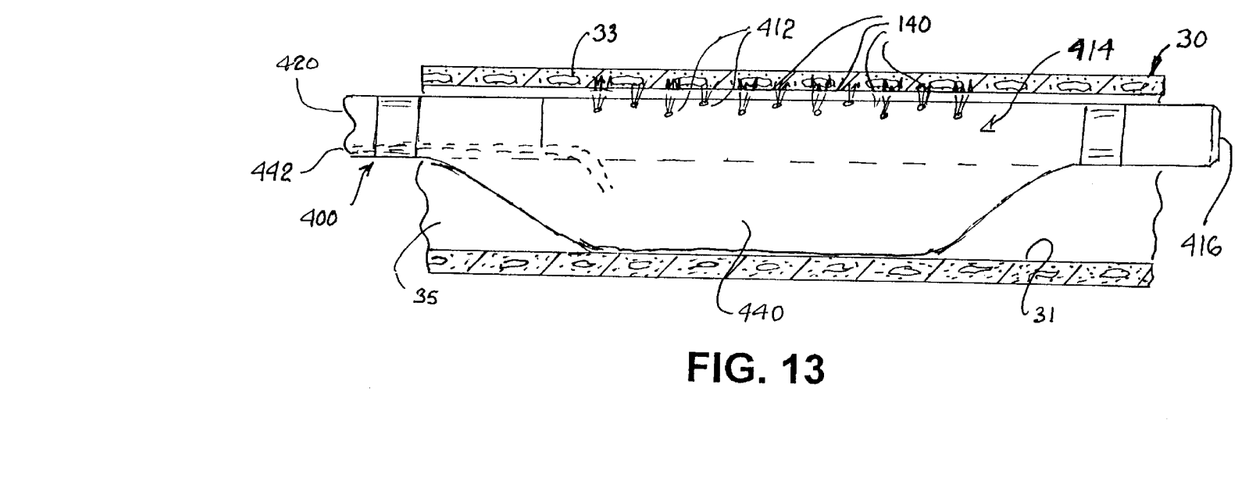

As disclosed in the above-referenced parent '487 patent application, the infusion catheter 10 as shown in FIG. 1 and infusion catheter 100 as shown in FIG. 9 are employed in a system of the type illustrated in FIG. 10 for delivering a thrombolytic agent, e.g. a plasminogen activator, through a catheter lumen and from a plurality of side wall perforations or infusion holes into a thrombus to dissolve it. The following description of FIGS. 1–10 follows the description of the same from the parent '487 application with additional references to the use of the catheters and system for infusing a substance as lining penetration jets into the walls of body vessels in accordance with the present invention. The body vessels include ducts, tracts and other vessels or organs, particularly blood vessels, and FIGS. 11a and 11b depict such infusion of a lining penetration infusate into arterial and venous blood vessel walls. FIGS. 12 and 13 depict embodiments of the infusion catheter to be employed in large diameter body vessels. These embodiments enable close positioning of the distal infusion segment, and particularly the infusion holes, against or close to the endothelial layer of the body vessel so that the lining penetration jets achieve penetration.

In a preferred embodiment of the invention, a distal end section 14 of the infusion catheter 10 is devised as shown in FIG. 1 for delivering an infusate comprising a thrombolytic agent, e.g. a plasminogen activator, for delivery into a thrombus or a lining penetration infusate for delivery into body vessel walls. The infusate is delivered through a catheter lumen 20 and from a plurality of side wall perforations or infusion holes 12 along a distal end infusion segment 14 just proximal to a distal end valve 16. The distal end valve 16 is of the type described in above-incorporated U.S. Pat. No. 5,085,635 that closes the distal end of the catheter lumen 20 and is penetrable by a guidewire (not shown) The catheter lumen 20 extends the length of the infusion catheter 10 from a connector assembly at its proximal end (not shown) of a type known in the art to the distal infusion segment 14 and the distal end valve 16. A guidewire (not shown) can be inserted through the catheter lumen 20 and through the distal end valve 16 to allow over the wire placement of the distal end infusion segment 14 in relation to a thrombus in a blood vessel, graft or other device. The proximal connector assembly is intended to be in fluid communication with a source of infusate. The plurality of infusion holes 12 in the infusion segment 14 allows the infusate to be delivered from the source through the infusion catheter lumen 20 and as power lysis jets into an adjacent thrombus or as lining penetration jets into an adjacent body vessel wall.

The infusion catheter 10 is formed with a side wall 22 that extends between the catheter lumen 20 and the catheter outer surface that is strong enough to withstand a relatively high pulsatile injection pressure applied from the infusate source to the infusate injected through the proximal connector assembly into the catheter lumen 20. The side wall 22 may be formed of any of the known polymeric materials enclosing a reinforcing wire braid or material to withstand bursting under the fluid pressure applied to the infusate within the catheter lumen 20.

In one preferred embodiment, the outer diameter of the catheter 10 in the infusion segment 14 is about 0.166 cm (4FR) the side wall thickness is about 0.035 cm, and the lumen diameter is about 0.099 cm.

The distal infusion segment 14 preferably commences about 0.5 cm proximal from the distal end valve 16 and extends proximally for a relatively short length of about 0.2 cm to about 1 cm. Proximal and distal radiopaque marker bands 24 and 26 are preferably provided at the proximal and distal ends of the infusion segment 14 in order to identify its location using fluoroscopy.

The plurality of side wall infusion holes 12 through side wall 22 are preferably arranged in a uniform or non-uniform pattern extending 360° around the catheter body in the distal infusion segment 14. The infusion holes 12 are preferably dense in the infusion segment 14, and the infusion segment 14 is relatively short. In the illustrated preferred embodiments of the invention, the plurality of infusion holes 12 are arranged in a spiral or helical pattern extending between the proximal and distal radiopaque marker bands 24 and 26. In this helical pattern, 20 to 32 infusion holes are preferably provided per cm of length of the infusion segment 14, depending on the pitch of the helical pattern.

The side wall perforations or infusion holes 12 are preferably about 0.01 cm (0.005 inches) in diameter. In FIG. 1, the infusion holes 12 are formed in a helical pattern that has a pitch determined by an offset of about 22.5° between adjacent infusion holes. Using a hole density of 32 holes per linear centimeter measured along the axial length of the infusion segment 14 results in a separation between is adjacent holes along the helical pattern of about 0.03 cm (0.0125 inches). If the hole density is reduced to 20 per linear centimeter and the same pitch is maintained, then the separation between adjacent holes along the helical pattern is about 0.05 cm (0.020 inches).

The side wall perforations or infusion holes 12 are relatively minute, and their size meters the ejection of the infusate therethrough. In the case of thrombolytic agents, a plasminogen activator based, thrombolytic agent is ejected therethrough as fine, high velocity, power lysis jets for lysing the adjacent thrombus as illustrated in FIGS. 2–4 and 6–8. A bolus of thrombolytic agent is injected by a power injector into the proximal connector assembly and catheter lumen 20 at a predetermined pressure and rate as described below that pressurizes the thrombolytic agent in the catheter lumen 20 and forces the fine, high velocity, power lysis jets out of the infusion holes 12 in a spiral pattern.

Figure 2:
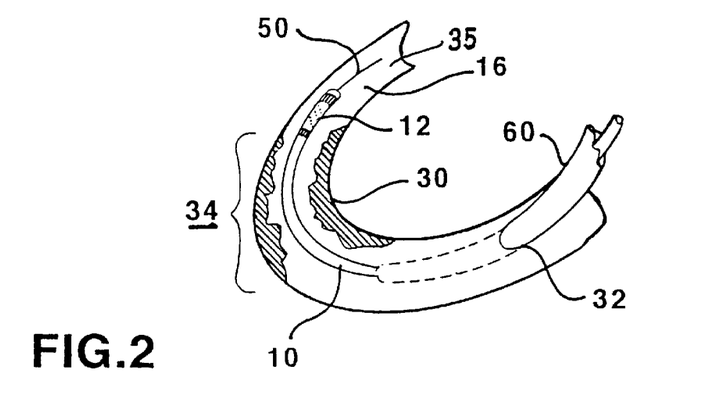
FIGS. 2–4 depict the use of the infusion catheter of FIGS. 1 and 9 to treat an elongated thrombus in a blood vessel.
Figure 3:
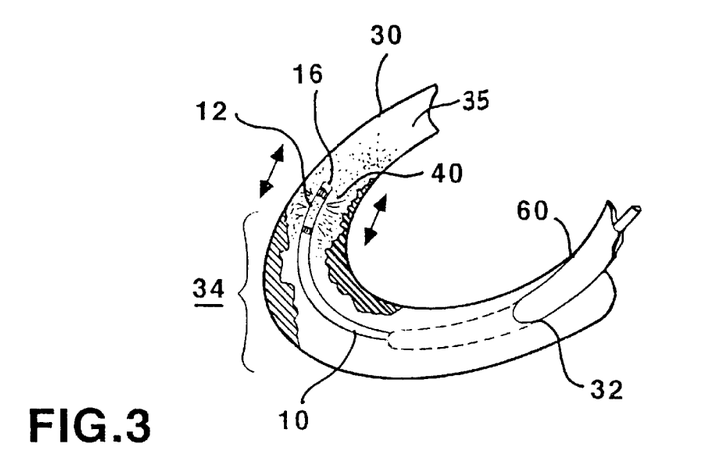
Figure 4:
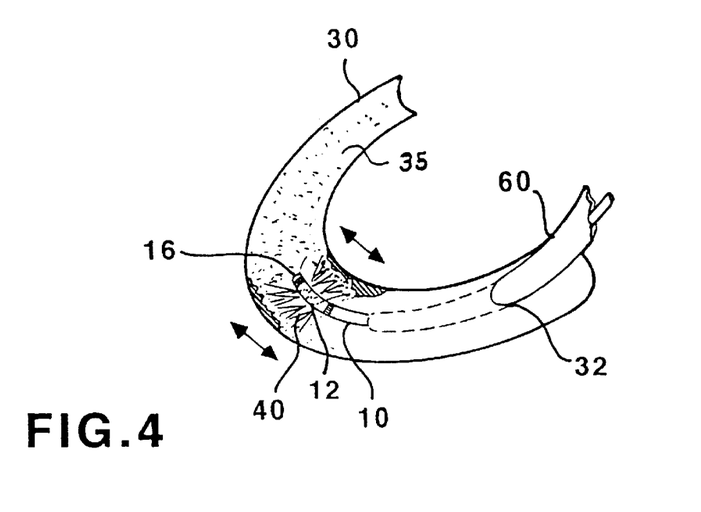

FIGS. 2–4 schematically illustrate steps in treating such an elongated thrombus 34 in the lumen 35 of a blood vessel 30. In FIG. 2, the catheter 10 is advanced through an introducer 60 and over a guidewire 50, both previously advanced through an opening 32 in the patient's skin and the vessel 30 that is distal to the distal end of the thrombus. The distal end valve 16 is penetrated by and slides over the guidewire 50 as the catheter 10 is advanced while being observed under fluoroscopy until the infusion segment 14 is located proximally past the proximal end of the thrombus 34. The guidewire 50 is retracted through the distal end valve 16 and the catheter lumen until it is removed from the connector end of the catheter 10 located outside the patient's body. The connector end of the catheter lumen is in fluid communication with a pulsatile fluid pump, e.g. a programmable power injector provided by Medrad, Inc., Indianola, Pa., under the trade name "Mark V" and Mark V Plus injection systems. These power injectors can be selectively adjusted to deliver an infusate from a source container into the lumen of a catheter at a selected flow rate and bolus volume or duration of each bolus. A limit can be set to limit the pressure of the infusate delivered into the catheter lumen, and the measured infusate pressure can also be displayed. Such power injectors are described in U.S. Pat. Nos. 4,370,982 and 5,520,653 to Reilly, for example.

In one example, 150 ml of a thrombolytic agent is prepared from a mixture of 250,000 units of urokinase, 40 ml of radiopaque contrast media, and the remainder of sterile saline for each 15 cm length (approximately) of the thrombus 34. The power injector is adjusted to deliver 5 ml of the thrombolytic agent to the catheter lumen at a rate of 25 ml/second. The power injector is set to a repeat mode to deliver the bolus at that rate once every 10 seconds, and the injection pressure of the mixture delivered into the catheter lumen is set to 600 psi. In FIG. 2, the power lysis jets 40 of the mixture are emitted in a spray extending in a spiral pattern around the infusion segment 14 in this embodiment employing infusion holes 12 arranged in a spiral pattern. It will be understood that the power lysis jets emitted by the more uniform pattern of infusion holes 12 of the first embodiment of FIG. 1 would form a somewhat more uniform spray. In either case, the back and forth movement of the catheter 10 by the physician tends to distribute the power lysis jets 40 within the surrounding section of the thrombus 34 to lyse it uniformly.

Then, in FIG. 3, the catheter 10 is retracted toward the opening 32 and into the proximal section of the thrombus 34. The physician optionally moves the catheter 10 back and forth slightly while each pulse of the thrombolytic agent is delivered. Progress in lysing the sections of the thrombus as the catheter 10 is moved is observed under fluoroscopy. The process continues to treat each section of the thrombus 34 as the catheter 10 is retracted toward the opening 32. It is expected that the 150 ml mixture will be consumed in thirty of the 5 ml pulsatile injections to treat a 20–30 cm length of thrombus over about a five minute time period. The mixture can be reloaded and the process continued for longer thrombus lengths.

At FIG. 4, the thrombus 34 is largely eliminated although fragments may remain attached to the blood vessel lining. After completing this power lysis method, the catheter 10 is retracted from the blood vessel lumen 35 through the lumen of the introducer 60. Finally, a post-lytic therapy regimen is followed to deliver a further quantity of thrombolytic agent over a longer period of time to completely dissolve the remaining fragments using a conventional infusion catheter of one of the types described above introduced into the blood vessel lumen 35. For example, a further quantity of thrombolytic agent is steadily delivered at a rate of 100,000 units per hour at low pressure from an IV pump along the length of the thrombus 34 for 12 hours while the patient rests.

In the use of the apparatus of the present invention as described above, the physician is able to see that the thrombus is being largely lysed as he/she manipulates the catheter 10 in FIGS. 3 and 4 and observes the fluoroscope. The lytic time spent by the physician is minimal, and the physician is afforded confidence that the treatment is working. The total time that the patient spends in the hospital or clinic during the lytic and post-lytic phases is about 12 hours which compares favorably to the 30 hours expended in the process described in the above-referenced Patel publication. In the example set forth above, the amount of thrombolytic agent is also reduced from more than 7,500,000 units in the above-referenced Patel publication to about 1,325,000 units for the 20–30 cm length thrombus. This reduction significantly reduces the total cost of the thrombolytic agent used in the treatment.

Figure 5:
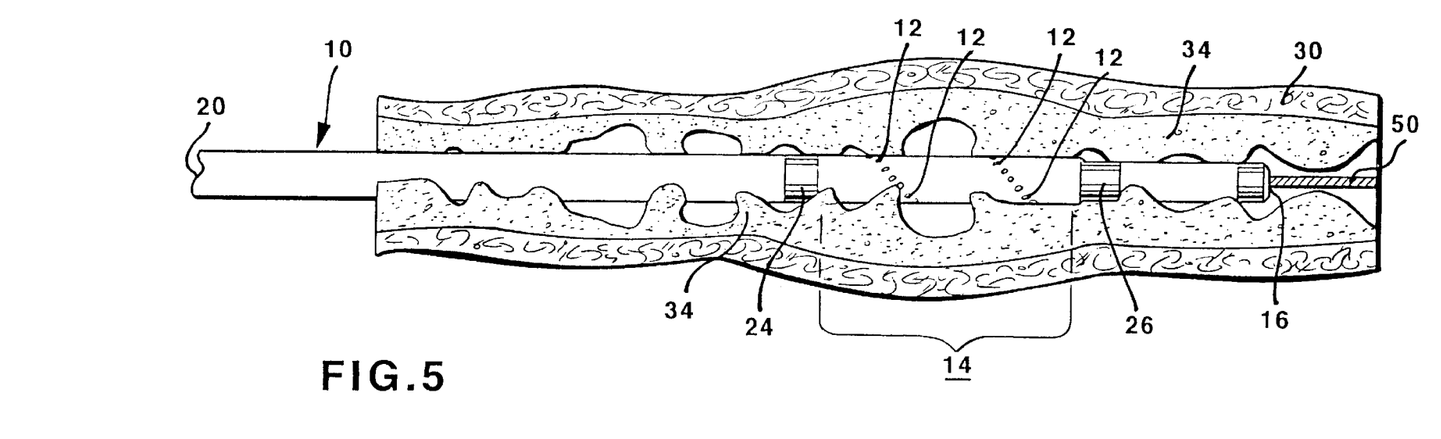
FIG. 5 is a more detailed view of the advancement of the infusion segment of the infusion catheter of FIGS. 1 and 9 over a previously placed guidewire into a thrombus section of an elongated thrombus in a blood vessel or medical device lumen.
Figure 6:
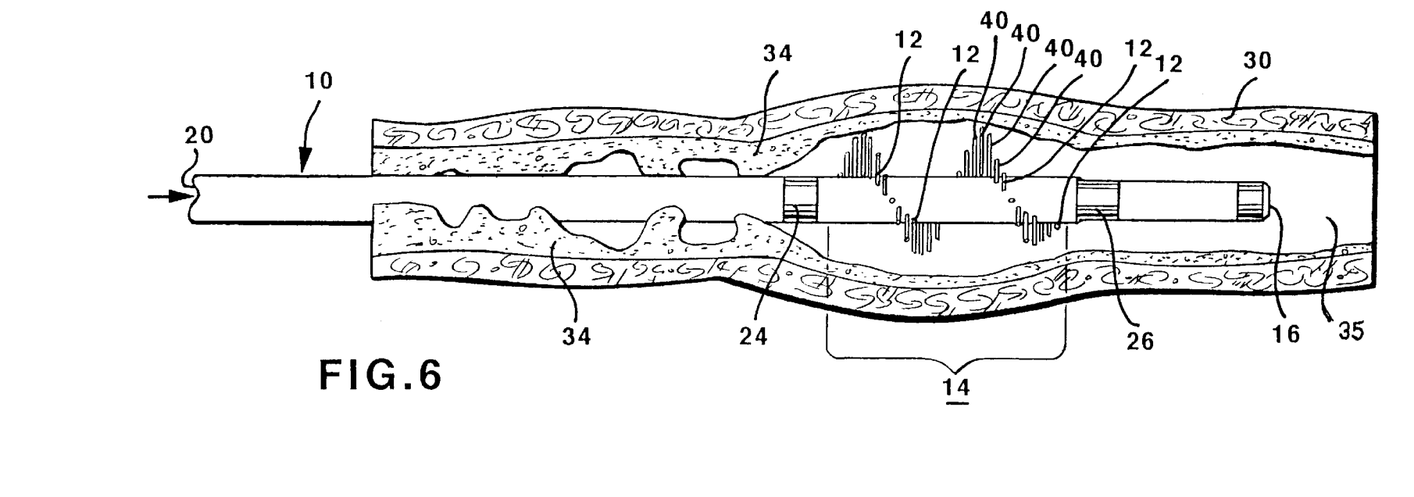
FIG. 6 is a view of the power lysis of the thrombus section of FIG. 5 with high velocity, power lysis jets emitted after withdrawal of the guidewire from the catheter lumen and closure of the distal end valve.
Figure 7:
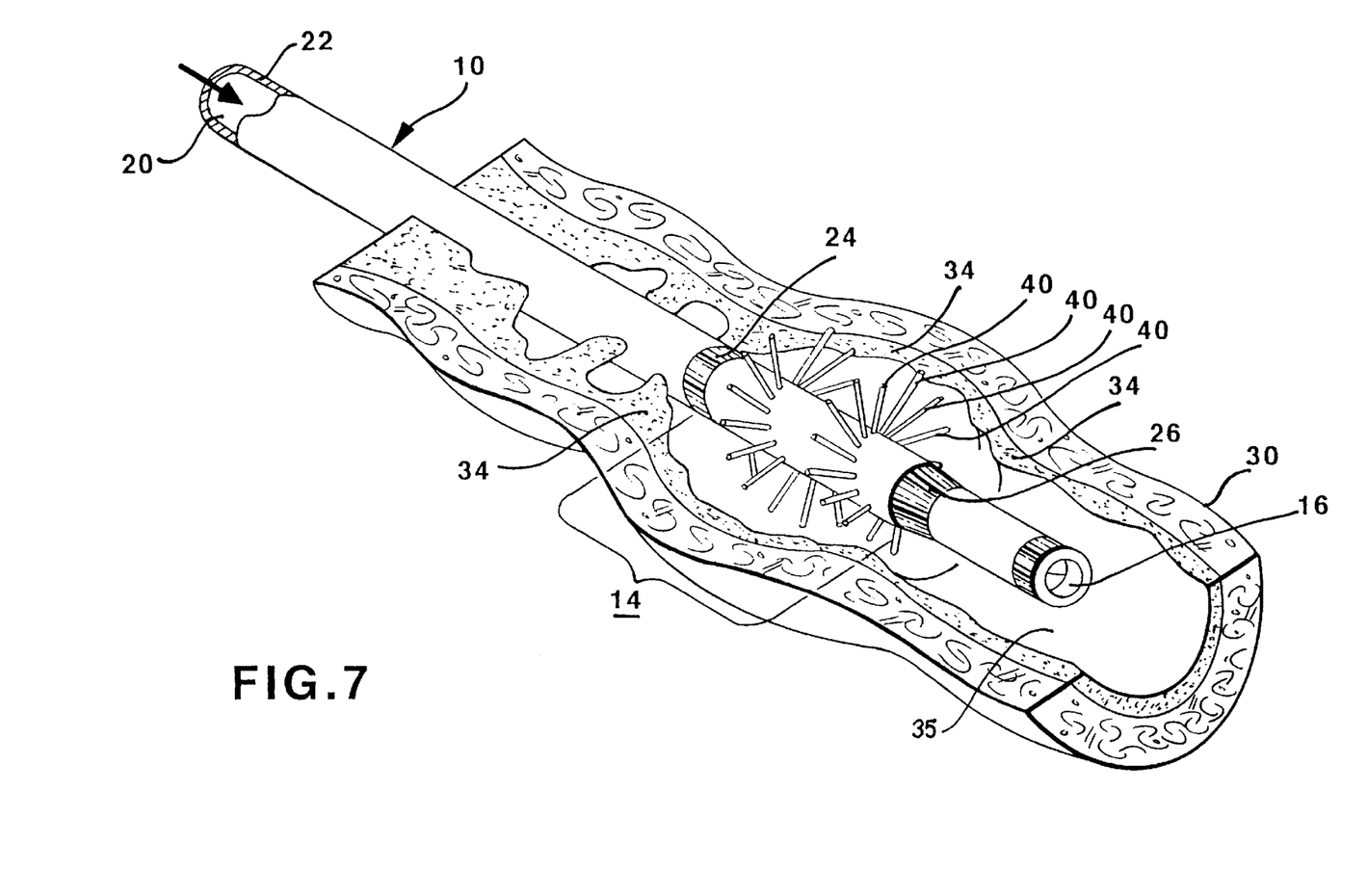
FIG. 7 is a perspective view of the pumping of thrombolytic agent from the infusion holes of the infusion catheter for power lysis to lyse the thrombus section of FIG. 5.
Figure 8:
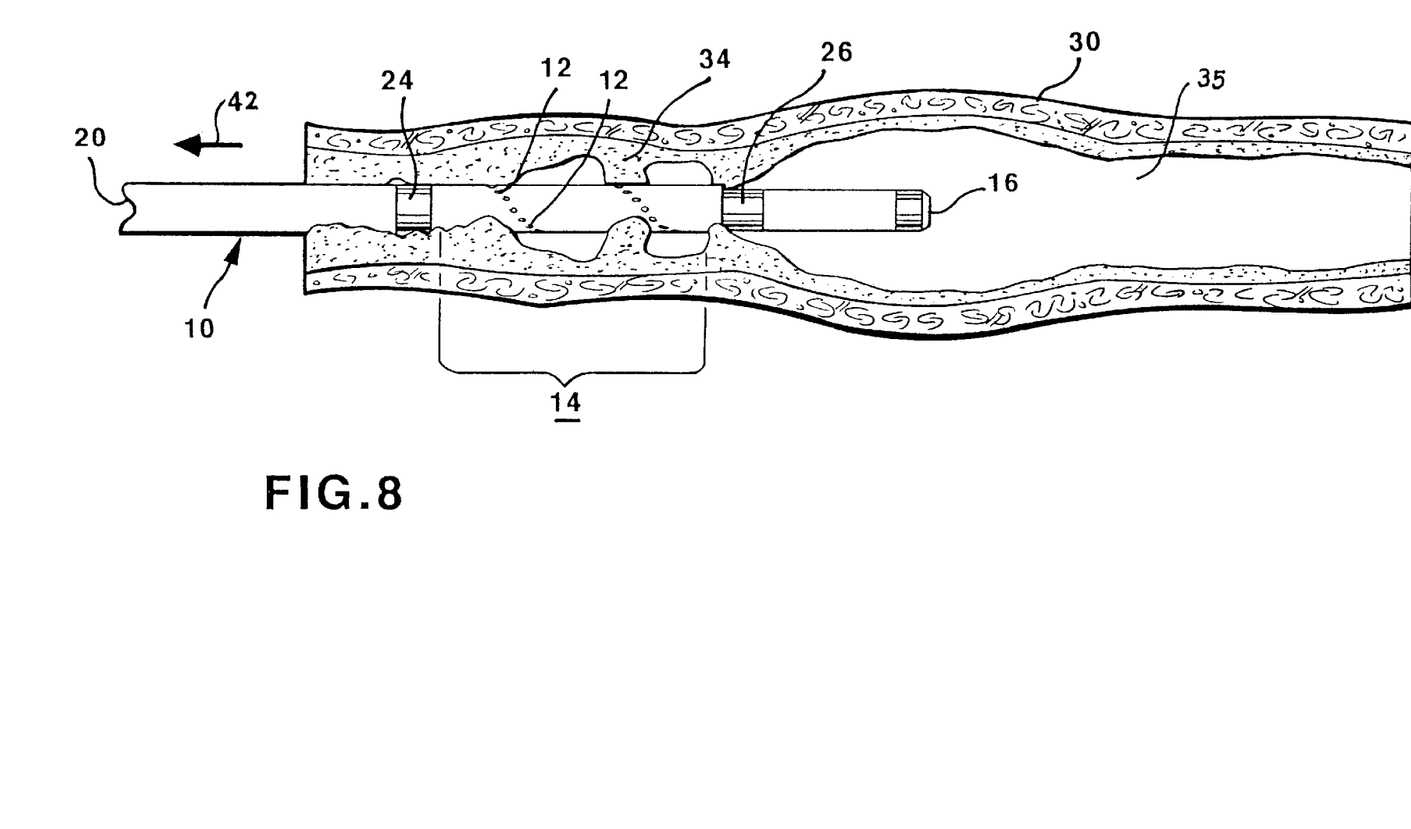
FIG. 8 is a more detailed view of the retraction of the infusion segment of the infusion catheter of FIGS. 1 and 9 over a previously placed guidewire into a more proximal thrombus section of the elongated thrombus to commence the power lysis of that section.

FIGS. 5–7 are more detailed views of the use of the power lysis catheter 10 to treat an elongated thrombus 34 in a blood vessel lumen 35. In FIG. 5, the catheter 10 is advanced to the position of FIG. 3, and in FIG. 6, the power lysis jets 40 are injected into the section of thrombus 34 surrounding the infusion segment 14. FIG. 7 is a perspective view of the pumping of thrombolytic agent from the infusion holes 12 of the power lysis catheter 10 in power lysis jets 40 to lyse the thrombin in a thrombus section of an elongated thrombus 34 in a blood vessel 30. The catheter 10 is preferably moved back and forth slightly during the emission of the power lysis jets to more thoroughly contact and lyse the thrombus section. In FIG. 8, the catheter 10 is retracted in the direction of arrow 42 to the next adjacent section of the thrombus 34 to repeat the injection of FIG. 6.

FIG. 9 is a perspective view of a infusion catheter 100 in accordance with a further embodiment of the present invention having a relatively uniform distribution of side wall infusion holes 112 formed in the distal infusion segment 114. In this embodiment, the infusion holes 112 are preferably evenly spaced apart and distributed along the length and 360° around the distal infusion segment 114 extending between proximal and distal radiopaque marker bands 124 and 126. In FIG. 9, for example, 30–50 side wall perforations or infusion holes 112 of about 0.01 cm (0.005 inches) in diameter may be formed per linear centimeter extending from the catheter lumen 120 through the catheter side wall 122. The plurality of side wall infusion holes 112 preferably extend proximally from about 0.5 cm from a distal end valve 116 for about 0.2 cm to 2.0 cm.

The infusion catheter 100 is otherwise constructed and used in the same manner as described above with reference to the infusion catheter 10. The infusion catheter 100 has at least one catheter lumen 120 extending the length thereof from a proximal end connector assembly (not shown) of a type known in the art to the distal end valve 116 that normally closes the distal end of the lumen catheter lumen 120. The distal end valve 116 is penetrable to allow a guidewire to be inserted through the lumen 120 and through the distal end valve 116 for over the wire placement of the distal end infusion segment 114 in relation to a thrombus (as shown in FIGS. 2 and 5 and described above). The catheter lumen 120 is also in fluid communication with a source of infusate at the proximal end of the catheter 100 for allowing the infusate to be delivered therethrough and emitted through the plurality of infusion holes 112 as power lysis jets or lining penetration jets.

FIG. 10 is a simplified schematic illustration of a pulsatile power injector system 200, e.g., the above-referenced power injector provided by Medrad, Inc., used with the preferred embodiments of the infusion catheter 10, 100 for practicing the methods of present invention. The system 200 includes a control console 202 that supports a pump or injector 206 and an infusate supply or source 210 on an extended arm 204 enclosing control cables from the control console 202. A display and command entry panel 208 on the console 202 allows the user to enter the control commands and observe displayed data. The command entry panel 208 is used to select the infusate pressure limit (in psi) within the catheter lumen, the volume of the bolus delivered (in ml) or the duration of delivery (in seconds), the rate of injection of the bolus (in ml/sec), the frequency of injection (times per minute). The power injector 206 is fitted with sensors for monitoring the infusate pressure within the catheter lumen and the bolus volume that is pumped into the catheter lumen, and a feedback system controls both parameters. The proximal connector end assembly 70 at the proximal end 72 of the infusion catheter 10, 100 is coupled with the power injector 206 and the infusate source 210.

In use of the depicted system 200 for power lysis of a thrombus, the catheter 10 or 100 is advanced through the access device in the opening 32 in the patient's skin and into the blood vessel or into the vascular device lumen and advanced over a previously introduced guidewire to the site of the thrombus as described above. The guidewire is withdrawn, and the catheter lumen 20 or 120 is filled with thrombolytic agent. The catheter lumen 20 or 120 is periodically pressurized as a bolus of thrombolytic agent is injected into the catheter lumen proximal end opening. A corresponding bolus of the thrombolytic agent is ejected as power lysis jets through the plurality of infusion holes 12 or 112 during the time that the bolus is applied under pressure to the catheter lumen. The method steps illustrated in FIGS. 2–4 and 5–8 are followed.

The fine, high velocity, power lysis, jets result from the injection of a bolus of thrombolytic agent having a prescribed fluid density at a selected pressure and injection rate of flow (volume per unit of time) into the catheter lumen which is controlled by a power injector 200. The outflow rate of thrombolytic agent from the infusion holes 12, 112 is proportional to the total number and size (i.e., the total outflow area) of the infusion holes in the infusion segment 14, 114, the pressure applied to the bolus as it is injected, and other factors. The injected bolus of thrombolytic agent injected into the catheter lumen 20, 120 forces a corresponding fraction of the bolus through each infusion hole 12, 112. The ejection velocity of the power lysis jets is related to the outflow rate and inversely proportional to the total outflow area. The outflow rate is selected to maximize the velocity of the high velocity, power lysis, jets of thrombolytic agent while maintaining the force of the jets below a force that would be sufficient to damage the blood vessel wall.

The ejection velocity or power lysis jet (or lining penetration jet) velocity can be found utilizing the following total fluid outflow (Q) and velocity (v) equations:

$$Q = C_d A \sqrt{2 P_{ex}/\rho} \quad (1)$$

and, after Q is determined using equation (1) or is determined out by the power injector:

$$V = Q/(C_v A) \quad (2)$$

where:

$C_v$ is the velocity coefficient which approaches 0.8–0.9 for the thrombolytic agent mixture identified above;

$C_c$ is the contraction coefficient of the infusion hole (for example, $C_c \approx 0.60$–0.70 for a sharp edged aperture);

$C_d$ is the discharge coefficient $C_d = C_c \times C_v$ (or $\approx 0.54$ for example);

$\rho$ is the fluid density ($\approx 1.2$ for the thrombolytic agent mixture described above);

$P_{ex}$ is the pressure head in excess of intervascular ambient pressure which is measured during delivery of the bolus and displayed by the power injector;

In practice, the total outflow Q is selected in ml/sec and the pressure head Pex is measured using the power injector 200. A power lysis jet (or lining penetration jet) velocity v of about 500–4000 inches/sec is calculated from these formulas using a pressure head $P_{ex}$ range of 30–900 psi and a total outflow area of about 0.25–0.50 mm$^2$.

The thrombolytic agent is delivered through the lumen of the catheter 10 at a pressure that well exceeds the pressure level employed in the above-described pulse-spray technique and is emitted through the infusion holes as relatively minute power lysis jets. These power lysis jets are sufficient to penetrate the thrombus but do not injure the vessel walls if they happen to contact the vessel walls. Moving the catheter back and forth slightly prevents a power lysis jet from dwelling too long in contact with a blood vessel and causes the contact with the thrombus to increase during the injection of each bolus of thrombolytic agent.

The thrombolytic agent is periodically pressurized at a higher frequency than once per minute as described in the above-referenced Bookstein et al. article so that the fine jets of thrombolytic agent are delivered more frequently. However, far less thrombolytic agent is delivered during each pulse and cumulatively over a comparable time period. The catheter 10 is advanced through the thrombus in the practice of the method of treating an elongated thrombus, e.g., an elongated DVT of the type described in the above-referenced Patel publication. As a result of these factors and techniques, the total time period of treatment is substantially shortened and the amount of delivered thrombolytic agent is substantially reduced.

The preferred embodiments of the invention may be employed to lyse a thrombus in a body blood vessel or in the blood flow lumen of an artificial graft, stent or vascular access device. In each case, the infusion segment is advanced into the thrombus, preferably in an over-the-wire procedure, and the thrombolytic agent is delivered as described above for each embodiment. The thrombolytic agent is delivered at high velocity in jets expelled outwardly of the catheter side walls, and the high velocity, power lysis jets lyse the adjacent thrombin of the thrombus.

The infusion catheters 10 and 100 can also be employed with the pulsatile power injector system 200 of FIG. 10 in the practice of a further aspect of the invention, that is, to infuse lining penetration infusates as lining penetration jets into the walls of body vessels. As noted above, the body vessels include ducts, tracts and other vessels or organs, particularly blood vessels. FIGS. 11a and 11b depict such infusion of lining penetration infusate into arterial and venous blood vessel walls.

In accordance with this aspect of the invention, the infusion catheter 10 or 100 is advanced through an introducer 60 and over a guidewire 50, both previously advanced through an opening 32 in the patient's skin and through the patient's arterial or venous system to a section of an artery or vein 30 to be treated in a manner akin to that illustrated in FIG. 2. The distal end valve 16 or 116 is penetrated by and slides over the guidewire 50 as the catheter 10 or 100 is advanced while being observed under fluoroscopy until the infusion segment 14 or 114 is located proximally past the section of the artery or vessel wall to be penetrated by the lining penetration jets. The guidewire 50 is retracted through the distal end valve 16 or 116 and the catheter lumen 20 or 120 until it is removed from the connector end of the catheter 16 or 100 located outside the patient's body. The connector end of the catheter lumen 20 or 120 is then coupled with the injector pump or injector 206 and the infusate supply or source 210 of FIG. 10. The display and command entry panel 208 on the console 202 allows the user to enter the control commands and observe displayed data. The command entry panel 208 is used to select the infusate pressure limit (in psi) within the catheter lumen, the volume of the bolus delivered (in ml) or the duration of delivery (in seconds), the rate of injection of the bolus (in ml/sec), the frequency of injection (times per minute).

In this way, a selected bolus volume of the lining penetration infusate) is injected at the selected flow rate into the high strength catheter lumen 20, 120 of the infusion catheter 10, 100. The corresponding bolus volume is ejected or emitted through multiple side wall perforations or infusion holes closely spaced from one another in the relatively short infusion segment as high velocity, low volume, lining penetration jets 140 as shown in FIGS. 11A and 11B that intramurally penetrate the adjacent endothelial layer 31 of vessel 30. The catheter infusion segment is advanced back and forth through the localized section of the vessel wall 30 of interest, and the high velocity intramural penetration of the adjacent endothelial layer 31 into the vessel wall 33 is repeated as necessary.

The fine, high velocity, lining penetration jets 140 result from the injection of a bolus of lining penetration infusate having a prescribed fluid density at a selected pressure and injection rate of flow (volume per unit of time) into the catheter lumen 20, 120 which is controlled by the power injector 206. The outflow rate of lining penetration infusate from the infusion holes 12, 112 is proportional to the total number and size (i.e., the total outflow area) of the infusion holes in the infusion segment, the pressure applied to the bolus as it is injected, and other factors. The injected bolus of lining penetration infusate injected into the catheter lumen forces a corresponding fraction of the bolus through each infusion hole as a lining penetration jet 140. The ejection velocity of the lining penetration jets 140 is related to the outflow rate and inversely proportional to the total outflow area. The outflow rate is selected to maximize the velocity of the high velocity, lining penetration jets of infusate to ensure penetration of the lining penetration infusate into the interior layers of the vessel wall 33.

As above, the infusion holes 12, 112 are dense in the infusion segment, and the infusion segment is relatively short, between 0.2 cm to 2.0 cm long, to provide a thorough coverage of the section of the endothelial layer of the wall of the vessel, duct, tract, or organ. For example, in one embodiment, 30 to 50 infusion holes are preferably provided per centimeter of length of the infusion segment and are evenly distributed around the circumference of the catheter body in each such cm of length. In another embodiment, the 20 to 32 infusion holes per linear centimeter are distributed in a helical pattern extending around the infusion segment and are closely spaced from one another. The high density spray of high velocity, lining penetration jets 140 causes the section of endothelial lining or layer 31 surrounding or adjacent to the short, 0.2 cm to 2.0 cm long, infusion segment to be thoroughly penetrated.

Certain other modifications in the design of the infusion catheters 10, 100 for the intramural delivery of lining penetration infusate may be desirable when the vessel lumen diameter exceeds the catheter diameter by a distance that causes the energy or force of the lining penetration jets 140 to be reduced when they impact the endothelial lining or layer 31. A first approach is to provide a selection of the infusion catheters 10, 100 having differing outer diameters, whereby an optimal relationship between infusion catheter outer diameter in the infusion segments 14, 114 and the vessel lumen diameter can be maintained. Secondly, the infusion catheters 10, 100 can be made available having differing lengths of the infusion segments 14, 114 and corresponding differing numbers of infusion holes 12, 112 distributed in the infusion segments 14, 114. Typically, the infusion catheter 10, 100 having a lesser number of infusion holes 12, 112 can be selected as the amount by which the vessel lumen exceeds the infusion catheter increases, so that, the velocity of the lining penetration jets 140 is increased if the injection pressure and bolus is maintained constant.

Another approach would be to provide a biasing mechanism of the infusion catheter to orient the infusion holes of the infusion segment closer to the endothelial layer 31. For, example, the infusion catheter disclosed in commonly assigned U.S. Pat. No. 5,554,114, incorporated herein by reference, having a coiled distal infusion segment when positioned in a vessel and having infusion holes oriented outward of the coil can be employed in the practice of the present invention. FIG. 12 depicts the distal portion of such an infusion catheter 300 formed into a loose coil providing a biasing mechanism to bias the infusion holes adjacent to or against the the endothelial layer 31 to ensure that the emitted lining penetration jets 140 penetrate through the endothelial layer 31 and into the vessel wall 33.

The proximal portion of the infusion catheter 300 is formed in the same manner as the proximal portion of infusion catheter 10 described in reference to FIG. 1. The expanded spiral coil, infusion configuration through the length of the distal infusion segment 314 can be effected in the manner of fabrication described in the above-incorporated '114 patent The distal infusion segment 314 of the infusion catheter 300 terminates with a penetrable valve 316 as described above and is straightened by a guidewire 50 as the infusion catheter 300 is advanced over the previously placed guidewire 50 in the manner depicted in FIG. 2. The core wire or guidewire 50 is shown in FIG. 12 being withdrawn from the lumen 320 of the infusion catheter 300. It will be understood that the proximal end of the infusion catheter 300 is then coupled to the injector 206 of the power injector system 200 of FIG. 10.

Thus, FIG. 12 is a partially sectioned view of the distal end of the infusion catheter 300 depicting its release from the straightened position of FIG. 2 into an expanded spiral coil, infusion configuration through the length of the distal infusion segment 314 and in relation to a vessel wall 30. The infusion ports 312 may be formed by slitting, puncturing or laser drilling the catheter sheath in the distal infusion segment 324 and are directed toward the endothelial layer 31 when the coil shape is assumed. The pressurized lining penetration infusate is conveyed through the infusion catheter lumen 320 to be forcefully emitted from the series of n infusion ports 312 through the catheter outer sheath in the distal infusion segment 314.

The expanded helical configuration may have an outer coil diameter on the order of 3–4 times the outer diameter of the sheath of the infusion catheter 300, which itself may have an outer diameter on the order of 0.014–0.038 inches. In this way, the helical coil turns of the distal infusion segment 314 may roughly expand to conform to the diameter of the vessel lumen 35. At the same time, fluid can flow in the direction of arrows 37 through the center of the loose, expanded helical coil configuration of the distal infusion segment 314 and through the vessel lumen 35. In the context of a blood vessel, the spiral coil expansion into the helical infusion segment 314 creates a blood perfusion lumen inside the coil turns that is disposed centrally in a blood vessel to allow and direct the laminar flow of blood therethrough in the direction of arrows 37 (or the reverse direction).

This coil configuration thus biases the infusion ports 312 located circumferentially on the outside of the spiral coil infusion segment 314 toward the endothelial layer 31, and the lining penetration jets 140 penetrate the endothelial layer a distance into the vessel wall 33 in the adjacent region. Also, the portion of the lining penetration infusate that does not penetrate the endothelial layer or otherwise escapes is distributed into a low blood flow rate, boundary layer region peripheral to the central laminar flow of blood or fluid and is kept there for a longer period to treat a damaged vessel wall.

Variations on the formation and maintenance of the coiled configuration of the distal infusion segment 314 described in the above-incorporated 114 patent may also be employed in the practice of the present invention. The overall length and number of infusion coil turns formed in the loose, expanded helical configuration of the distal infusion segment 314 may be varied. A core-wire coupled to the distal end of the infusion catheter may be substituted for the guidewire 50 and valve 316 and used to maintain the coiled configuration and/or vary its overall length as described therein.

The distal end portion of a further infusion catheter 400 having a further biasing mechanism 440 in its biasing state for maintaining close relation of the infusion holes 412 to the vessel 30 is depicted in FIG. 13. The distal infusion segment 414 of the infusion catheter 400 terminates with a penetrable valve 416 as described above. The biasing mechanism 440 is straightened into a non-biased state as described below, and the infusion catheter 400 is advanced over a previously placed guidewire 50 in the manner depicted in FIG. 2. It will be understood that the proximal end of the infusion catheter 400 is then coupled to the injector 206 of the power injector system 200 of FIG. 10 and the biasing mechanism is operated to assume the biasing state depicted in FIG. 13.

In these embodiments of FIG. 13, the infusion holes 412 extending into the catheter lumen 420 are formed in the same size and density as described above but only in the arcuate catheter wall section opposite to the direction of expansion of the expandable mechanism 440 and not all the way around the catheter body circumference. The proximal portion of the infusion catheter 400 is formed in the same manner as the proximal portion of infusion catheter 10 described in reference to FIG. 1, except for side port mechanisms for placing the biasing mechanism in its biasing and non-biasing states.

The biasing mechanism 440 can comprise an inflatable balloon along one side of the catheter body in the distal infusion segment 414 coupled to a balloon inflation lumen 442 extending alongside the lining penetration infusate delivery and guidewire receiving catheter lumen 420 to a side port of the proximal connector assembly (not shown). Such balloon constructions are depicted, for example, in commonly assigned U.S. Pat. No. 5,795,331, incorporated herein by reference. The balloon biasing mechanism 440 can be constructed to provide a perfusion path as also described in the '331 patent.

In this embodiment, the expanded balloon biases the infusion ports 412 of the infusion segment 414 toward the endothelial layer 31, and the lining penetration jets 140 penetrate the endothelial layer a distance into the vessel wall 33 in the adjacent region. The portion of the lining penetration infusate that does not penetrate the endothelial layer or otherwise escapes is distributed into the low blood flow rate, boundary layer region and is kept there for a longer period to treat a damaged vessel wall. The distal infusion segment 414 may be successively rotated about the axis of the catheter body within the vessel lumen 35 to apply the lining penetration jets 140 to the endothelial layer 31 all the way around the vessel lumen 35.

Alternatively, the biasing mechanism 440 may comprise an expandable member, e.g. a wire, that is attached to the distal end of the catheter body and extends outwardly therefrom alongside the distal infusion segment 414 and then enters the lumen 442 and extends proximally and loosely through the lumen 442 to a point of the proximal connector assembly. The distal section of the wire bridging the distal infusion segment 414 is adapted to be pushed out of and extended away from the catheter body alongside the distal infusion segment 414 or drawn into the lumen 442 and close to the distal infusion segment 414 by application of pushing and pulling forces to its proximal end at the proximal connector assembly.

In all of the above-described and equivalent embodiments, the lining penetration infusate preferably includes the a radiopaque material that can be observed under fluoroscopy as it is emitted from the infusion holes as fine, high velocity, lining penetration jets 140. The catheter infusion segment 14, 114, 314, 414 can be advanced back and forth in the section of the endothelial layer 31 by the physician manipulating the proximal portion of the catheter 10, 100, 200, 300 400 during the emission of the lining penetration jets 140 as described above with respect to the thrombus to distribute the intramurally delivered lining penetration infusate more evenly. The distribution of the radiopaque, lining penetration infusate can be observed under fluoroscopy or other radiographic imaging. either in a stand alone procedure or following an earlier procedure, e.g. an angioplasty or atherectomy procedure using a separate balloon catheter previously introduced over the straight infusion device 10.

The preceding specific embodiments are illustrative of the practice of the invention. It is to be understood, therefore, that other expedients known to those of skill in the art or disclosed herein may be employed without departing from the invention or the scope of the appended claims. It is therefore to be understood, that within the scope of the appended claims, the invention may be practiced otherwise than as specifically described without actually departing from the spirit and scope of the present invention.

What is claimed is:

1. An intramural substance delivery system for delivering a therapeutic or diagnostic lining penetration infusate as a plurality of lining penetration jets through a body vessel wall lining and intramurally into the body vessel wall comprising:
   an infusion catheter having a side wall and catheter lumen extending between a catheter proximal end and a catheter distal end, an elongated infusion segment having a plurality of closely spaced apart, infusion holes in said side wall that extend from said catheter lumen to the outer surface, said spaced apart infusion holes having a diameter of about 0.01 cm and distributed over a length of the infusion segment of about 0.2 cm to about 2.0 cm in a helical pattern and in a density of 20–32 infusion holes per centimeter length of said helical pattern, and a valve in said catheter distal end that is normally closed to close the catheter lumen distal end and penetrable by a guidewire for receiving said guidewire and allowing advancement of said infusion catheter over the guidewire to orient the infusion segment side wall of the infusion catheter with respect to a section of the body vessel wall and for allowing withdrawal of the guidewire proximally from said valve to allow said valve to close and from said catheter lumen to allow said catheter lumen to be filled with the lining penetration infusate; and
   means for injecting a predetermined bolus of the lining penetration infusate at a predetermined rate into said catheter lumen at a pressure that effects ejection of the lining penetration infusate at high velocity through said infusion holes as fine lining penetration jets of lining penetration infusate to mechanically penetrate the lining of the vessel wall.

2. The intramural delivery system delivery system of claim 1, wherein said injecting means further comprises a pulsatile fluid pump and a supply of therapeutic or diagnostic substance coupled to said catheter lumen at the catheter proximal end.

3. The intramural delivery system of claim 2, wherein said injecting means further comprises means for injecting a bolus of about 5 ml of therapeutic or diagnostic substance at a rate of about 25 ml per second into said catheter lumen at a pressure that effects ejection of the therapeutic or diagnostic substance through said plurality of infusion holes as said lining penetration jets.

4. The intramural delivery system of claim 2, wherein said injecting means further comprises means for injecting a bolus of about 5 ml of therapeutic or diagnostic substance at a rate of about 25 ml per second into said catheter lumen at a pressure of about 30–900 psi that effects ejection of the therapeutic or diagnostic substance through said infusion holes and for repeating the injecting step about once every 10 seconds.

5. The intramural delivery system of claim 2, wherein said injecting means further comprises means for injecting a bolus of about 5 ml of therapeutic or diagnostic substance at a rate of about 25 ml per second into said catheter lumen at a pressure of about 30–900 psi that effects ejection of the therapeutic or diagnostic substance through said infusion holes to achieve a lining penetration jet velocity of about 500–4000 inches/sec.

6. The intramural delivery system of claim 1, wherein said injecting means further comprises means for injecting a bolus of about 5 ml of therapeutic or diagnostic substance at a rate of about 25 ml per second into said catheter lumen at a pressure that effects ejection of the therapeutic or diagnostic substance through said plurality of infusion holes as said lining penetration jets.

7. The intramural delivery system of claim 1, wherein said injecting means further comprises means for injecting a bolus of about 5 ml of therapeutic or diagnostic substance at a rate of about 25 ml per second into said catheter lumen at a pressure of about 30–900 psi that effects ejection of the therapeutic or diagnostic substance through said infusion holes and for repeating the injecting step about once every 10 seconds.

8. The intramural delivery system of claim 1, wherein said injecting means further comprises means for injecting a bolus of about 5 ml of therapeutic or diagnostic substance at a rate of about 25 ml per second into said catheter lumen at a pressure of about 30–900 psi that effects ejection of the therapeutic or diagnostic substance through said infusion holes to achieve a lining penetration jet velocity of about 500–4000 inches/sec.

9. The intramural delivery system of claim 1, wherein said infusion catheter further comprises a biasing mechanism operable in a biasing state for biasing said side wall and at least certain ones of said infusion holes of said infusion segment into close relation with the section of the vessel wall and in a non-biasing state for enabling advancement of said infusion catheter over said guidewire to orient said side wall of the infusion catheter in said infusion segment with respect to the section of the body vessel wall and for enabling withdrawal of said infusion catheter from the body vessel.

10. The intramural delivery system of claim 9, wherein said biasing mechanism comprises an asymmetric balloon adapted to be inflated laterally of said infusion segment in said biasing state with an inflation fluid, thereby biasing said side wall and at least certain ones of said infusion holes of said infusion segment into close relation with the section of the vessel wall.

11. The intramural delivery system of claim 9, wherein said biasing mechanism comprises an expandable wire adapted to be extended laterally of said infusion segment side wall in said biasing state, thereby biasing said side wall and at least certain ones of said infusion holes of said infusion segment into close relation with the section of the vessel wall.

12. The intramural delivery system of claim 1, wherein said distal infusion segment is formed with a biasing mechanism to assume a coiled infusion configuration when extended in a body vessel lumen in a biasing state for biasing said side wall and at least certain ones of said infusion holes of said infusion segment into close relation with the section of the vessel wall and a straight infusion configuration in a non-biasing state for enabling advancement of said infusion catheter over said guidewire to orient said side wall of the infusion catheter in said infusion segment with respect to the section of the body vessel wall and for enabling withdrawal of said infusion catheter from the body vessel.

13. An intramural substance delivery system for delivering a therapeutic or diagnostic lining penetration infusate as a plurality of lining penetration jets through a body vessel wall lining and intramurally into the body vessel wall comprising:

an infusion catheter having a side wall and catheter lumen extending between a catheter proximal end and a catheter distal end, an elongated infusion segment having a plurality of closely spaced apart, infusion holes in said side wall that extend from said catheter lumen to the outer surface, and a valve in said catheter distal end that is normally closed to close the catheter lumen distal end and penetrable by a guidewire for receiving said guidewire and allowing advancement of said infusion catheter over the guidewire to orient the infusion segment side wall of the infusion catheter with respect to a section of the body vessel wall and for allowing withdrawal of the guidewire proximally from said valve to allow said valve to close and from said catheter lumen to allow said catheter lumen to be filled with the lining penetration infusate; and means for injecting a bolus of about 5 ml of therapeutic or diagnostic substance at a rate of about 25 ml per second into said catheter lumen at a pressure that effects ejection of the therapeutic or diagnostic substance through said plurality of infusion holes as fine lining penetration jets of lining penetration infusate to mechanically penetrate the lining of the vessel wall.

14. The intramural delivery system of claim 13, wherein said infusion catheter further comprises a biasing mechanism operable in a biasing state for biasing said side wall and at least certain ones of said infusion holes of said infusion segment into close relation with the section of the vessel wall and in a non-biasing state for enabling advancement of said infusion catheter over said guidewire to orient said side wall of the infusion catheter in said infusion segment with respect to the section of the body vessel wall and for enabling withdrawal of said infusion catheter from the body vessel.

15. The intramural delivery system of claim 14, wherein said biasing mechanism comprises an asymmetric balloon adapted to be inflated laterally of said infusion segment in said biasing state with an inflation fluid, thereby biasing said side wall and at least certain ones of said infusion holes of said infusion segment into close relation with the section of the vessel wall.

16. The intramural delivery system of claim 14, wherein said biasing mechanism comprises an expandable wire adapted to be extended laterally of said infusion segment side wall in said biasing state, thereby biasing said side wall and at least certain ones of said infusion holes of said infusion segment into close relation with the section of the vessel wall.

17. The intramural delivery system of claim 14, wherein said distal infusion segment is formed with a biasing mechanism to assume a coiled infusion configuration when extended in a body vessel lumen in a biasing state for biasing said side wall and at least certain ones of said infusion holes of said infusion segment into close relation with the section of the vessel wall and a straight infusion configuration in a non-biasing state for enabling advancement of said infusion catheter over said guidewire to orient said side wall of the infusion catheter in said infusion segment with respect to the section of the body vessel wall and for enabling withdrawal of said infusion catheter from the body vessel.

18. The intramural delivery system delivery system of claim 13, wherein said injecting means further comprises a pulsatile fluid pump and a supply of therapeutic or diagnostic substance coupled to said catheter lumen at the catheter proximal end.

19. The intramural delivery system of claim 13, wherein said injecting means further comprises means for injecting the bolus of about 5 ml of therapeutic or diagnostic substance at the rate of about 25 ml per second through said infusion holes into said catheter lumen at a pressure of about 30–900 psi.

20. The intramural delivery system of claim 13, wherein said injecting means further comprises means for injecting the bolus of about 5 ml of therapeutic or diagnostic substance at a rate of about 25 ml per second through said infusion holes into said catheter lumen at a pressure of about 30–900 psi that effects ejection of the therapeutic or diagnostic substance at a lining penetration jet velocity of about 500–4000 inches/sec.

21. The intramural delivery system of claim 13, wherein said injecting means further comprises means for injecting the bolus of about 5 ml of therapeutic or diagnostic substance at the rate of about 25 ml per second through said infusion holes into said catheter lumen at a pressure of about 30–900 psi and means for repeating the injecting step about once every 10 seconds.

22. The intramural delivery system of claim 13, wherein said injecting means further comprises means for injecting the bolus of about 5 ml of therapeutic or diagnostic substance at a rate of about 25 ml per second through said infusion holes into said catheter lumen at a pressure of about 30–900 psi that effects ejection of the therapeutic or diagnostic substance at a lining penetration jet velocity of about 500–4000 inches/sec and means for repeating the injecting step about once every 10 seconds.

* * * * *